(12) United States Patent
Seto et al.

(10) Patent No.: US 6,706,683 B1
(45) Date of Patent: Mar. 16, 2004

(54) METHOD FOR CONTROLLING THE RELEASE OF GRANULES

(75) Inventors: Minoru Seto, Sizuoka (JP); Kouichirou Fukuda, Sizuoka (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 09/806,382
(22) PCT Filed: Sep. 28, 1999
(86) PCT No.: PCT/JP99/05302
§ 371 (c)(1),
(2), (4) Date: Mar. 29, 2001
(87) PCT Pub. No.: WO00/18970
PCT Pub. Date: Apr. 6, 2000

(30) Foreign Application Priority Data

Sep. 29, 1998 (JP) .......................................... 10/274574

(51) Int. Cl.[7] .......................... C12N 15/16; C12N 5/06; A61K 33/00
(52) U.S. Cl. .......................... 514/2; 435/69.4; 435/7.1; 435/7.21; 435/7.24; 435/406; 424/198.1; 424/604
(58) Field of Search .................................. 435/7.1, 7.21, 435/7.24, 69.4, 406; 530/300; 514/2; 424/198.1, 604

(56) References Cited

U.S. PATENT DOCUMENTS 5,350,687 A 9/1994 Odink et al.
5,702,920 A 12/1997 Odink et al.

FOREIGN PATENT DOCUMENTS

EP 0 263 072 A2 4/1988

OTHER PUBLICATIONS

Hessian P. A. et al. (2001)The heterodimeric complex of MRP–8 (S100A8) and MRP–14 (S100A9). Antibody recognition, epitop definition and the implications for structure. Eur J Biochem. vol. 268, pp. 353–363.*

Propper, C. et al. (1999) Analysis of the MRP8–MRP14 protein–protein interaction by the two–hybrid system suggests a prominent role of the C–terminal domain of S100 proteins in dimer formation. J Biol Chem. vol. 274, pp. 183–188.*

Ngo, J. T. et al. et al. (1994) "Computational complexity protein structure prediction, and the levinthal paradox". in "The protein folding problem and tertiary structure prediction". p. 491–495, Merz, Jr. K. et al. Eds. Birkhauser, Boston.*

Burmeister et al. *Immunobiol.*, vol. 171, pp. 461–474 (1986).

(List continued on next page.)

Primary Examiner—Karen Cochrane Carlson
Assistant Examiner—Samuel W. Liu
(74) Attorney, Agent, or Firm—Young & Thompson

(57) ABSTRACT

A method of controlling granule secretion comprising performing a treatment to increase or decrease an active form of calgranulin on a cell line having capability of secreting granules, thereby increasing or decreasing granule secretion from the cell line.

A method of detecting a substance which inhibits or activates the granule secretion reaction by applying this controlling method. An active form of calgranulin is increased by making the cells permeabilized cells and adding a calgranulin and soluble calcium. Decrease of an active form of calgranulin is carried out by introducing a calgranulin antibody into cells.

The method is useful for screening a substance which inhibits or activates granule secretion.

18 Claims, 3 Drawing Sheets

OTHER PUBLICATIONS

Murao. *Acta Histochem. Cytochem.*, vol. 27, No. 2, pp. 107–116 (1994).

Oyama et al. *Biochemical and biophysical research Communications*, vol. 240, pp. 341–347 (1997).

Dell'Angelica et al. *The Journal of Biological Chemsitry*, vol. 269, No. 46, Issue of Nov. 18, pp. 28929–28936, (1994).

Lagasse et al. *Molecular and Cellular Biology*, vol. 8, No. 6, pp. 2402–2410, (Jun. 1998).

Murao et al. *The Journal of Biological Chemistry*, vol. 264, No. 14, Issue of May 15, pp. 8356–8360 (1989).

Geczy. *Biochimica et Biophysica Acta*, vol. 1313, pp. 246–252, (1996).

Murthy et al. *The Journal of Immunology*, vol. 151, No. 11, pp. 6291–6301, Dec. 1, 1993.

Gottsch et al. *Tr. Am. Opth. Soc.*, vol. XCV, pp. 111–129, (1997).

* cited by examiner

METHOD FOR CONTROLLING THE RELEASE OF GRANULES

TECHNICAL FIELD

The present invention relates to a method of controlling secretion of granules from cell lines having granule secretion capability, preferably secretion of granules from neutrophils and to a method of detecting substances which inhibit or activate the granule secretion reaction based on the method of controlling secretion of granules.

BACKGROUND ART

Neutrophils play an important role in the defense of a living body. A major function of neutrophils is to migrate into bacteria and microorganisms which invade into living bodies and eat the bacteria and microorganisms, thereby rendering a sterilizing effect. In one sterilization mechanism of neutrophils, sterilization is effected after fusion of phagosomes and granules by the action of bactericidal proteins and proteases which are present in the granules. Although bactericidal proteins and proteases which are present in neutrophils are important sterilization substances, their excessive production and secretion are known to injure intima of blood vessels (Fahey, T. J. et al., In Update Pulmonary Diseases and Disorders (Fishman A P, ed) (1992) MacGraw-Hill, New York).

Intimal injury of blood vessels is deeply concerned with the occurrence of diseases such as adult respiratory distress syndrome (ARDS) (Weiland, J. E. et al., Am. Rev. Respir. Dis. (1986) 133: 218–225), injury by reperfusion after ischemia (Cavanagh, S. P. et al. Cardiovasc. Surg. (1998) 6: 112–118), glomerular nephritis (Jennette, J. C. and Falk, R. J., Am. J. Kidney Dis. (1994) 24: 130–141), cystic fibrosis (Greenberger, P. A., J. A. M. A (1997) 278: 1924–1930), rheumatoid arthritis (Chang, D. J. et al. Semin. Arthritis Rheum. (1996) 25: 390–403), chronic bronchitis (Hoidal, J. R., Semin. Respir. Infect. (1994) 9: 8–12), spasm of blood vessel (Merhi, Y. et al. Arterioscler. Thromb. (1993) 13: 951–957), asthma (Borson, D. B. et al. Am. J. Physiol. (1991) 260: L212–L225), peripheral circulation disorder and angina pectoris (Merhi, Y. et al. Arterioscler. Thromb. (1993) 13: 951–957), hypertension (Dz au, V. J., Am. J. Med. (1984) 77: 31–36), arteriosclerosis (Belch, J. J., Curr. Opin. Lipidol. (1994) 5: 440–446), and the like. Therefore, the substances which inhibit secretion of neutrophil granules are thought to be useful as a therapeutic drug for treating diseases associated with secretion of neutrophil granules. Genes which control secretion of neutrophil granules are also thought to make genetic therapy of diseases associated with secretion of neutrophil granules possible.

However, the mechanism of secretion of neutrophil granules is not yet elucidated at present. An increase in the calcium concentration in neutrophils is known to be indispensable for secretion of granules. However, no molecules which are activated by an increase in the calcium concentration and induce granule secretion are known. Therefore, there have been no specific neutrophil secretion inhibitors developed so far, nor any genetic therapy targeting the inhibition of neutrophil secretion inhibitors practiced.

The study for specifying intra neutrophil molecules which are activated by the increase in the calcium concentration and researching compounds and genes which inhibit such molecules are expected to contribute to the development of an effective preventive and/or treating agent, and curative method for diseases associated with secretion of neutrophil granules such as adult respiratory distress syndrome (ARDS), injury by reperfusion after ischemia during acute myocardial infarction, glomerular nephritis, cystic fibrosis, rheumatoid arthritis, chronic bronchitis, cerebral vasospasm, asthma, peripheral circulation disorder, angina pectoris, hypertension, arteriosclerosis, and the like.

There are three types of calgranulins: calgranulin A (Burmeister, G., Immunology (1986) 171: 461–474) (named as S100A8, MRP8, p8, or L1 light chain), calgranulin B (Burmeister, G., Immunology (1986) 171: 461–474) (named as S100A9, MRP14, 14 or L1 heavy chain), and calgranulin C (Dell' Angelica, E. C., J. Biol. Chem. (1994) 269: 28929–28936) (named as S100A12 or p6).

Calgranulin A is a calcium-binding protein with a molecular weight of about 8 kD, calgranulin B is a calcium-binding protein with a molecular weight of about 14 kD, and calgranulin C is a calcium-binding protein with a molecular weight of about 10 kD and classified in the S100 protein.

Calgranulin A and calgranulin B were cloned by E. Lagasse et al. and their whole amino acid sequences were reported in 1988 (E. Lagasse and R. G. Clerc, Molc. Cellular. Biol. (1988) No. 8, 2402–2410). Calgranulin A and calgranulin B are present specifically in neutrophils and monocytes and occupy about 5% of all proteins in neutrophils or monocytes.

As a finding suggesting intracellular physiological functions of calgranulins, the action of calgranulin A and calgranulin B inhibiting the activity of casein kinases I and II has been reported (Murao S. et al. J. Biol. Chem (1989) 264: 8356–8360).

However, physiological functions of casein kinases I and II in neutrophils and monocytes are still to be clarified. This inhibitory effect is not dependent on the calcium concentration. Therefore, the physiological function through the activity control of casein kinases I and II by calgranulin A and calgranulin B is not known at the present. As the findings suggesting extracellular physiological functions of calgranulins, the function of calgranulin A to increase migration of neutrophils and monocytes (Geczy, C. L., Biochim. Biophys. Acta (1996) 1313: 246–253) and the antibacterial activity of calgranulin A and calgranulin B (Murthy, A. R. K. et al., J. Immunol. (1993) 151: 6291–6301) have been reported.

However, the only calgranulin which exhibits neutrophil/monocyte migration activity is mouse calgranulin A. Thus, this is not a physiological activity common to other warm-blooded animals including humans. The antibacterial activity of calgranulin A and calgranulin B is due to their capability of trapping divalent metals in a solution essential for the growth of bacteria. The activity would not be a physiological function specific to calgranulins.

Only little is known about physiological functions of calgranulin A and calgranulin B at the present time. The action of calgranulin A and calgranulin B to control secretion of neutrophil or monocyte granules has not been known at all. Calgranulin C was cloned by J. D. Gottsch et al. and its whole amino acid sequence was reported in 1997 (Gottsch, J. D. et al., Trans. Am. Ophthalmol. Soc. (1997) 95: 111–125). Calgranulin C is known to be present in granulocytes, but whether calgranulin C is present in other cells is not known. Neither, is its function known. Thus, the effect of calgranulin C on the control of the mechanism of neutrophil or monocyte granule secretion has not been known.

DISCLOSURE OF THE INVENTION

An object of the present invention is to provide a method of controlling secretion of granules of cell lines having granule secretion capability, and a method of detecting substances which inhibit or activate the reaction of granule secretion based on the method of controlling secretion of granules.

As a result of extensive studies to achieve the above objective, the inventors of the present invention have found that secretion of granules can be controlled in the following manner. Specifically, if a treatment to increase the amount of active form of calgranulin is carried out on a cell line having the capability of secreting granules, the cell line increases secretion of granules; and if a treatment to decrease the amount of active form of calgranulin is carried out, granule secretion from the cell line decreases. This finding has led to the completion of the present invention.

Specifically, the present invention provides a method of controlling granule secretion which comprises performing a treatment to increase or decrease an active form of calgranulin on a cell line having the capability of secreting granules.

The cell line having granule secretion capability used herein is not specifically limited inasmuch as the cell line can secrete granules. Neutrophils originating from warm-blooded animals or neutrophil-like cells can be given as preferable examples. Neutrophils originating from warm-blooded animals are also called neutrophilous leukocytes, neutrophilic leukocytes, heterophilic leukocytes, or polymorphonuclear leucocytes. Neutrophil-like cultured cells are cultured cells containing at least one type of granule included in neutrophils. HL60 cells that can be differentiated into granulocytes by a suitable treatment using retinoic acid, dimethylsulfoxide, or the like can be given as specific examples. Neutrophils can be separated from blood of the warm-blooded animals or cells which move into the abdominal cavity by stimulation such as intraperitoneal administration of casein (Biological Chemistry Experiment Lecture, second series, No. 8 Blood, Vol. 2, 679–685). Cultured leukemia cell strains which can be differentiated into granulocytes are used after induction into neutrophil-like cells by differentiation using a suitable inductor of differentiation (Biological Chemistry Experiment Lecture, second series, No. 8 Blood, Vol. 1, 117–123).

Calgranulins are present in warm-blooded animals, for example. Calgranulin A (named as S100A8, MRP8, p8, or L1 light chain) and calgranulin B (named as S100A9, MRP14, p14 or L1 heavy chain) are known. Human-type calgranulin A and human-type calgranulin B were cloned and their whole amino acid sequences have been reported (E. Lagasse and R. G. Clerc, Molc. Cellular. Biol. (1988) No. 8, 2402–2410). Mouse-type calgranulin A and mouse-type calgranulin B were cloned and their whole amino acid sequences have been reported (E. Lagasse and I. L. Weissman, Blood (1992) 79: 1907–1915)3. Mouse-type calgranulin A and mouse-type calgranulin B show a high homology of amino acid sequence to those of humans. Specifically, their homology to the human-type calgranulin A and human-type calgranulin B, respectively, is about 60%. Calgranulin A and calgranulin B which are present in various warm-blooded animals are thought to exhibit comparatively small difference in the amino acid sequence among animals. Therefore, in the calgranulin of the present invention the amino acid, sequences exhibiting about 60% or more homology to the amino acid sequence of human calgranulin A or B are included in the preferable peptides as long as the amino acid sequences possess the following preferable activity.

In the present invention, a calgranulin exhibiting activity is specially referred to as an active form of calgranulin. Specifically, such activity may be any activity based on calgranulin A or calgranulin B, and this can be easily confirmed by the following measuring method of calgranulin activity.

Specifically, the calgranulin activity can be easily confirmed and determined by using the method shown in Example 1 or 2. The permeabilized neutrophil suspension prepared by the method of Example 1 is added to a 96-well immuno plate and incubated at 30–40° C. for 5–30 minutes. After simultaneous or successive addition of a water-soluble calcium compound and a substance having calgranulin activity to the well, the calgranulin activity is determined by measuring the amount of substances secreted in the supernatant, such as elastase or lactoferrin, according to the method of Example 1 or 2.

In a normal case, an active form of calgranulin is produced by binding calgranulin and calcium.

Homologues or mixtures of calgranulins are also included in the calgranulin of the present invention.

Homologues of calgranulin A or calgranulin B are mutants, fragments, and derivatives of the calgranulins possessing calgranulin activity. The mutants indicate calgranulins exhibiting the same activity as the calgranulin A or calgranulin B, but formed by a natural or artificial gene manipulation technique on a DNA level, for example, by the site specific mutagenesis, in which a part of amino acids is replaced, deleted, or added (PAS, 75, pp 4268–4270 (1978), Necl. Acid. Res., 6, pp 2973–2985 (1979), Genetic Engineering Principle and Methods, Vol. 3, pp 1–32 (1981), etc.).

The fragments mean fragments of calgranulin A or calgranulin B which contains continuous amino acids.

The derivatives mean calgranulin A or calgranulin B in which the functional group such as an amino group, hydroxyl group, mercapto group, or carboxyl group is modified by, for example, glycosylation, acylation, amidation, or esterification. The derivatives further include dimers of calgranulin A or calgranulin B, their mutants, or fragments in which the mercapto group of cysteine residue is oxidized to the disulfide form providing intermolecular S-S linkages, as well as mixed dimers produced from calgranulin A, its mutant, or fragment and calgranulin B, its mutant, or fragment which are bound through an oxidized mercapto group of cysteine residue, all exhibiting the calgranulin activity.

There are no limitations to the mixtures inasmuch as the mixture is a mixture of calgranulin A or its homologue and calgranulin B or its homologue at an arbitrary ratio and exhibits the calgranulin activity.

The amino acid sequence of calgranulin A is shown by (SEQ ID NOS 1 and 3) of the Sequence Table (Nature (1987) 330 (5) 80–82), and the amino acid sequence of calgranulin B is shown by (SEQ ID NOS 2 and 4) of the Sequence Table (the same source). Therefore, calgranulins including at least one of the following peptides can be given as preferable active form of calgranulins of the present invention.

(i) A peptide consisting of the amino acid sequence 1–93 encoded by Sequence ID No. 1 of the Sequence Table and binding calcium thereto.

ii) A peptide consisting of the amino acid sequence 1–114 encoded by Sequence ID No. 2 of the Sequence Table and binding calcium thereto.

iii) A peptide having an amino acid sequence in which one or more amino acids are deleted from or added to the amino acid sequence encoded by Sequence ID No. 1 or 2 of the Sequence Table, or one or more amino acids in the amino acid sequence encoded by Sequence ID No. 1 or 2 are replaced with other amino acids, binding calcium thereto, and exhibiting the activity of increasing secretion of granules of cell lines having granule secretion capability.

The following methods can be given as examples of the method of increasing an active form of calgranulin in cell lines having granule secretion capability.

a) A method of converting cell membranes of cell lines having granule secretion capability, preferably neutrophils or neutrophil-like cultured cells into permeabilized cell membranes, and simultaneously or successively adding a calgranulin and a water-soluble calcium compound.

b) A method of simultaneously or successively adding a calgranulin and a water-soluble calcium compound to a cell line having granule secretion capability by microinjection using a very fine injection needle.

c) A method of mixing a calgranulin and a water-soluble calcium compound, enclosing the mixture in a liposome, and causing the mixture to contact with a cell line having granule secretion capability, thereby fusing cell membranes.

d) A method of introducing a calgranulin gene into a cell line having granule secretion capability to cause calgranulin to over expression and adding a water-soluble calcium compound to the expressed calgranulin.

To change the membrane of a cell line having granule secretion capability into a permeabilized cell membrane, cells having granule secretion capability are first separated from blood, for example and prepared. Any known method of separation and preparation may be used for preparing such cells. The cells having granule secretion capability may be suspended cells or may occasionally be adhered cells. Suspended cells are more preferable in the present invention in view of ease of separation from blood. Cells having granule secretion capability separated from blood are suspended and stored in a physiological saline solution or a phosphate buffered saline.

When used, the suspension is re-suspended in a buffer solution containing potassium chloride and sodium chloride such as a HEPES buffer solution or Tris buffer solution, for example, incubated, and processed to convert the membranes into permeabilized cell membranes. A buffer solution containing 50–200 mM potassium chloride and 5–30 mM sodium chloride is preferable as the buffer solution containing potassium chloride and sodium chloride used in the present invention. Specific examples are a 10–50 mM HEPES (pH 6.5–7.5) buffer solution or a 10–50 mM Tris (pH 6.5–7.5) buffer solution. The mixture is incubated at 4–40° C. for 10–60 minutes.

The cells having granule secretion capability separated from blood are incubated in a RPMI 1640 medium, MEM (Minimum Essential Medium) medium, or the like which contains fetal bovine serum. Suspended cells are re-suspended in the buffer solution containing potassium chloride and sodium chloride. In the case of adhered cells, supernatant of the culture liquid is discarded and cells are re-suspended in the buffer solution containing potassium chloride and sodium chloride. The suspension is incubated in the same manner as described above and processed to make the membranes permeabilized cell membranes.

The cells having granule secretion capability obtained in this manner are subjected to a treatment to make the membranes permeabilized cell membranes. One example of this treatment comprises treating the cells with an agent having a function of making holes through the membranes by acting on part of the cell membranes such as, for example, a surfactant, bacterial toxin, or glycerol. As examples of surfactants, digitonin, saponin, octylphenol-polyethyleneglycolether (Triton X-100), 3-[(3-cholamidopropyl)dimethylammoniol]-1-propane-sulfonate (CHAPS), polyoxyethylene (20) cetylether (Brij 58), and the like can be given. As examples of bacterial toxins, α-toxin, streptolysin-O, and the like can be given. An amount of 0.01 $\mu$M to 1000 mM of the above agent is added to $1 \times 10^7$ cells/ml, and the mixture is incubated at 4–40° C. for 5–120 minutes.

Treatment of cells using short electric pulses (an electroporation method) is another preferable method of forming permeabilized cell membranes. Specifically, an amount of $1 \times 10^7$ cells/ml of cell line is treated with 1–10 KV (kilovolt) electric pulses at 4–40° C. for 1–30 minutes.

A method of using laser beams, a method of using a hypotonic solution, and the like are also preferable methods of forming permeabilized cell membranes.

The water-soluble calcium compound used in the present invention is not specifically limited inasmuch as the compound produces calcium ions when it contacts with water. Powders or aqueous solutions of calcium acetate, calcium carbonate, and calcium chloride are given as examples. A particularly preferable water-soluble calcium compound is a compound which produces calcium ions at a concentration of 100 mM or more when the compound contacts with water. When an aqueous solution is used, its calcium concentration is preferably 100 mM or more.

Simultaneous addition of a calgranulin and a water-soluble calcium compound to permeabilized cell membranes in the present invention means a procedure of previously mixing the calgranulin and water-soluble calcium compound, incubating the mixture to make the calgranulin active form of, and adding the active form of calgranulin. Successive addition of a calgranulin and a water-soluble calcium compound means a procedure of separately adding the calgranulin and water-soluble calcium compound irrespective of the order of addition.

The amount of calgranulin added is usually 0.01 $\mu$M or more, and preferably 0.1–5 $\mu$M. Although there is no specific upper limit, an amount less than 10 $\mu$M is preferable. In the same manner, the amount of water-soluble calcium compound added is usually 0.01 $\mu$M or more, and preferably 0.1–5 $\mu$M. Although there is no specific upper limit, the amount less than 10 $\mu$M is preferable.

Incubation is carried out usually at 4–40° C. Incubation is carried out usually for 5–30 minutes.

The other methods of increasing an active form of calgranulin in cell lines having granule secretion capability will now be described.

Cells having granule secretion capability are first separated from blood, and suspended and stored in a physiological saline or a phosphate buffered saline as mentioned above. Alternatively, the cells are cultured in a RPMI medium, MEM medium, or the like containing fetal bovine serum. In the case of suspended cells, the cells are suspended in a culture medium. In the case of adhered cells, the cells are need for microinjection, introduction of liposomes, genes, and the like.

Although microinjection is carried out according to a conventional method, the use of a very fine injection needle with a diameter of usually 1 $\mu$M or less, preferably 0.1–0.8 $\mu$M, is desirable. Such an injection needle can be prepared by extending a molten glass capillary. Specifically, an injection needle is set in a manipulator controllable within an accuracy of 1 µM, and a calgranulin and a soluble calcium compound are simultaneously microinjected into the cells. Alternatively, the calgranulin is microinjected first and, after a while, for example after 1–60 minutes, preferably after 3–10 minutes, the water-soluble calcium compound is microinjected. It is possible to microinject calgranulin after microinjection of the water-soluble calcium compound. In this instance, the concentrations of the calgranulin and water-soluble calcium compound may be approximately the same as the above described concentrations.

In the method of increasing an active form of calgranulin in a cell line having granule secretion capability by membrane fusing using a liposome, the calgranulin and a water-soluble calcium compound are mixed and enclosed in the liposome, and caused to contact with the cells, thereby fusing cell membranes. First, a phospholipid solution containing cholesterol, for example, a mixture of egg yolk phosphatidylcholin, dimyristoyl phosphatidic acid, and cholesterol at a molar ratio of 4:1:5 is prepared. A water-soluble calcium compound and calgranulin are added to the mixture, and the resulting mixture is stirred and filtered through a membrane filter, for example, a membrane filter made of Teflon, thereby obtaining an emulsion. The emulsion is subjected to a rotary evaporator to evaporate an organic solvent, and calgranulin which is not enclosed in the liposome is removed. As the method of removal, a 12% sucrose density-gradient centrifugation is preferably used. In this manner, calgranulin is mixed with a water-soluble calcium compound and converted into an active form of calgranulin, and a liposome in which the active form of calgranulin is enclosed prepared. Next, the liposome with an active form of calgranulin is enclosed therein is caused to contact with the above-mentioned cells having granule secretion capability. For example, the liposome is added to $1 \times 10^5 \sim 1 \times 10^7$ cells in a concentration of 0.01–100 µM, and preferably 0.1–10 µM, and the mixture is incubated. Incubation is carried out at 4–40° C. for 1–30 minutes, for example. In this manner, membranes are fused and an active form of calgranulin can be increased in the cell lines having granule secretion capability.

As a method of causing calgranulin to over-expression, a method of recombining a gene encoding calgranulin in a known plasmid vector or virus vector, and introducing the recombinant into the cells can be given. The polynucleotide sequence shown as Sequence ID No. 1 or No. 2 in the sequence table, for example, can be used as a gene encoding calgranulin. The recombinant vector can be introduced into the cells by the calcium phosphate method, the DEAE dextran method, lipofectin method, electric pulse method, or the like. The above-described various methods may be preferably used for introducing a calgranulin gene in a cell line and causing the calgranulin to over-expression. The cells are converted to cells having the above-mentioned permeabilized cell membrane and a water-soluble calcium compound is preferably introduced in the cell line. Specifically, a calgranulin gene is introduced into cells by incubating a plasmid vector or virus vector in which the calgranulin gene has been incorporated in the amount of the 1–200 µg per $0.5 \times 10^7$ to $3 \times 10^7$ cells at 4–40° C. for 5–120 minutes together with 1–100 µg of calcium phosphate, 0.1–10 mg of DEAE dextran, or 1–100 µg of lipofectin, or by treating the plasmid vector or virus vector in which the calgranulin gene has been incorporated in the amount of the 1–200 µg per $0.5 \times 10^7$ to $3 \times 10^7$ cells using a short electric pulse at 4–40° C. for 1–30 minutes. The above-mentioned various methods may be used for introducing the water-soluble calcium compound.

The following methods can be given as examples of the method of decreasing active form of calgranulin of cell lines having granule secretion capability.
a) A method of converting a cell line having granule secretion capability into cells with permeabilized cell membranes and adding a calgranulin antibody.
b) A method of adding calgranulin antibody to a cell line having granule secretion capability by microinjection using a very fine injection needle.
c) A method of enclosing a calgranulin antibody in a liposome and causing the liposome to act on a cell line having granule secretion capability, thereby fusing cell membranes.
d) A method of introducing an anti-sense gene for a calgranulin gene into a cell line having granule secretion capability, thereby knocking out calgranulin.

A monoclonal antibody to calgranulin can be prepared by the method described in Am. J. Physiol. 274, C1563–C1572 (1988). For example, 10–100 µg of calgranulin is mixed with a complete Freund's adjuvant and intraperitoneally administered in a mouse. After administration several times, once every two weeks, the spleen is excised to prepare spleen cells. The spleen cells are fused with myeloma cells using polyethylene glycol and cultured in an HAT medium containing 15% fetal bovine serum, to select only fused cells. At the time when colonies are identified by the naked eye, calgranulin antibody-producing cells are confirmed by the ELISA method in which the calgranulin is combined with a 96 well immuno plate, and cloning is carried out by the limiting dilution method. The cells obtained are cultured and the monoclonal antibody to calgranulin produced in the supernatant is collected.

The monoclonal antibody to calgranulin is also available from BMA Company.

To obtain a polyclonal antibody to calgranulin, 10–100 µg of calgranulin is mixed with a complete Freund's adjuvant and subcutaneously administered to a rabbit. After administration several times, once every two weeks, blood is collected to obtain a polyclonal antibody as antiserum.

The calgranulin antibody is added to the cells having granule secretion capability having permeabilized cell membranes prepared by the above-mentioned method in an amount of 1–100 µg per $1 \times 10^5$ to $1 \times 10^7$ cells, for example, and the mixture is incubated at 4–40° C. for 1–30 minutes, whereby the calgranulin antibody is introduced into the cells.

Microinjection is another method of introducing calgranulin antibody into cell lines, wherein 0.01–10 µg of the calgranulin antibody is introduced into the cells by microinjection using an injection needle set in a manipulator under pressure by an injector.

Still another method comprises enclosing 1–100 µg of the calgranulin antibody into the above-mentioned liposome, adding the liposome to the cells at a concentration of 0.01–100 µM, preferably 0.1–10 µM, per $1 \times 10^5$ to $1 \times 10^7$ cells, and incubating the mixture at 4–40° C. for 1–30 minutes.

A calgranulin anti-sense gene can be obtained by inserting a gene having a base sequence complementary to the base sequence shown by (SEQ ID NOS 1 or 2), for example. In the present invention, a plasmid vector or virus vector is prepared by inserting 1–200 _g of this calgranulin anti-sense gene per $0.5 \times 10^7$ to $3 \times 10^7$ cells. The resulting vector is incubated at 4–40° C. for 5–120 minutes with the addition of 1–100 g of calcium phosphate, 0.1–10 mg of DEAE dextran, or 1–100 _g of lipofectin. Alternatively, a plasmid vector or virus vector with 1–200 g of the calgranulin anti-sense gene inserted per $0.5 \times 10^7$ to $3 \times 10^7$ cells is added and treated by a short electric pulse at 0.05–0.5 kV at a temperature of 4–40° C. for 1–30 minutes.

In this manner, an anti-sense gene for a calgranulin gene is introduced into a cell line having granule secretion capability and knocked out.

A treatment of increasing or decreasing an active form of calgranulin in cell lines having granule secretion capability can be carried out according to the above-described procedure. As a result, granule secretion of a cell line can be controlled by increasing or decreasing granule secretion of the cell line.

Granule secretion of neutrophils is known to injure intima of blood vessels as mentioned above. Injury of blood vessel intima is known to be deeply associated with diseases such as adult respiratory distress syndrome (ARDS), injury by reperfusion after ischemia during acute myocardial infarction, glomerular nephritis, cystic fibrosis, rheumatoid arthritis, chronic bronchitis, cerebral vasospasm, asthma, peripheral circulation disorder, angina pectoris, hypertension, arteriosclerosis, and the like. Therefore, a curative agent, improving agent, or improving method may be provided when granule secretion is decreased in the above method for controlling secretion of granule. A gene therapy for diseases and phenomenon associated with secretion of neutrophil granules, such as adult respiratory distress syndrome (ARDS), injury by reperfusion after ischemia during acute myocardial infarction, glomerular nephritis, cystic fibrosis, rheumatoid arthritis, chronic bronchitis, cerebral spasm, asthma, peripheral circulation disorder, angina pectoris, hypertension, arteriosclerosis, and the like, may be possible if an anti-sense gene for a calgranulin gene is recombined in virus vector introducing the resultant recombinant gene into neutrophils removed from a patient and returning the cells to the patient. Specifically, the above-described granule secretion control method includes a curative method and improving method of the above diseases.

The present invention also provides a method of detecting a substance which inhibits or activates the granule secretion reaction.

Specifically, the present invention provides a method of detecting a substance which inhibits or activates the granule secretion reaction comprising the following steps:

A) A step of increasing an active form of calgranulin in cell lines having granule secretion capability;

B) A step of causing a sample which may contain a substance inhibiting or activating the granule secretion reaction (hereinafter simply referred to as "sample") to contact with the cell lines having granule secretion capability, and incubating the mixture; and C) A step of detecting the subject substance secreted from the cell line.

The step B) for causing the sample to contact with the cell lines having granule secretion capability may be carried out before, after, or during step A) for increasing an active form of calgranulin.

The method of detecting a substance which inhibits or activates the granule secretion reaction of the present invention includes a method of quantitative determination of the substance or a method of screening the substance.

The same procedure as described above can be employed in the method of conducting step A) to increase active form of calgranulin of cell lines having granule secretion capability. Specifically, the following methods can be given:

a) A method of converting cell membranes of cell lines having granule secretion capability, preferably neutrophils or neutrophil-like cultured cells, into permeabilized cell membranes, and simultaneously or successively adding a calgranulin and a water-soluble calcium compound.

b) A method of simultaneously or successively adding a calgranulin and a water-soluble calcium compound to a cell line having granule secretion capability by microinjection using a very fine injection needle.

c) A method of mixing a calgranulin and a water-soluble calcium compound, enclosing the mixture in a liposome, and causing the mixture to come into contact with a cell line having granule secretion capability to fuse cell membranes.

d) A method of introducing a calgranulin gene into a cell line having granule secretion capability to cause the calgranulin to be over-expressed and adding a water-soluble calcium compound to the expressed calgranulin.

In the step B) of causing a sample which may contain a substance inhibiting or activating the granule secretion reaction to contact with the cell lines having granule secretion capability, and incubating the mixture, biological components, naturally occurring substances, compounds, and the like can be given as examples of the sample. This procedure of causing the sample to contact with the cell lines having granule secretion capability is carried out before, after, or during step A) of increasing an active form of calgranulin. As the cell lines having granule secretion capability, the said cell line having granule secretion capability itself, a cell line in which the calgranulin has been increased, a cell line in which the active form of calgranulin has been increased, and the like can be used. The former two cell lines increase an active form of calgranulin by the above-mentioned treatment for increasing the active form of calgranulin.

In a preferable method of increasing an active form of calgranulin, the calgranulin is first increased in the cell line having granule secretion capability and then a water-soluble calcium compound is increased in this cell line, or an active form of calgranulin produced by reacting a calgranulin with a water-soluble calcium compound is increased in the cell line having granule secretion capability. This sample is caused to contact with the cell line before, after, or during the procedure of increasing the calgranulin or active form of calgranulin. The procedure of contacting the sample with the cell line is preferable as a method of screening pharmaceutical agents without a treatment in which the sample is penetrated through cell membranes.

A specific example is as follows. In the case where permeabilized cell membranes are used, an appropriate concentration of the sample which may contain a substance inhibiting or activating the granule secretion reaction is added to the cell suspension and the mixture is incubated. In this instance, 1–100 $\mu$M of the sample is added to a suspension of neutrophils or neutrophil-like cultured cells having permeabilized cell membranes, and the mixture is incubated at 4–40° C. for 1–30 minutes. Next, a calgranulin is added, and after a while, a water-soluble calcium compound is added. For example, the water-soluble calcium compound is added 1–60 minutes, and preferably 3–10 minutes, after the addition of calgranulin. In this instance, the calgranulin and water-soluble calcium compound are added in the amount of about 0.01–10 $\mu$M each and preferably 0.1–3 $\mu$M each. The order of the addition may be either first calgranulin and then water-soluble calcium compound, or first the water-soluble calcium compound and then the calgranulin. The most preferable method is first preparing an active form of calgranulin by the reaction of a calgranulin and a water-soluble calcium compound, then adding the active form of calgranulin into the above mentioned cell line. The sample may be added to the cell line not only before the addition of the calgranulin, but also simultaneously or after the addition of the calgranulin or active form of calgranulin. The reaction for granule secretion is initiated in this manner.

In the case where cells having granule secretion capability, for example, neutrophils or neutrophil-like cultured cells are injected by microinjection, an appropriate concentration, for example, 1–100 μM, of the sample which may contain a substance inhibiting or activating the granule secretion reaction is added to the neutrophils or neutrophil-like cultured cells, and the mixture is incubated at 4–40° C. for 1–30 minutes. A calgranulin is microinjected at an appropriate concentration, for example, at 0.01–10 μM, and preferably 0.1–3 μM, and a water-soluble calcium compound is microinjected simultaneously at a concentration, for example, at 0.01–10 μM, and preferably 0.1–3 μM. Alternatively, the water-soluble calcium compound is microinjected after microinjection of calgranulin, for example after 1–60 minutes, preferably after 3–10 minutes, whereby the granule secretion reaction is initiated.

In the case where neutrophils or neutrophil-like cultured cells are reacted with a liposome, a sample which may contain a substance inhibiting or activating the granule secretion reaction is added to the suspension of the neutrophils or neutrophil-like cultured cells at an appropriate concentration, 1–100 μM, for example, and the mixture is incubated for 1–30 minutes. A calgranulin is previously mixed with a water-soluble calcium compound at a concentration of, for example, 0.01–10 μM, and preferably 0.1–3 μM, and the mixture is incubated, for example, at 4–40° C. for 1–30 minutes, then introduced into a liposome at a concentration of 0.01–101 μM, and preferably 0.1–3 μM. The liposome is added into a suspension of neutrophils or neutrophil-like cultured cells to initiate the granule secretion reaction.

In the case of using cells in which the calgranulin is over-expressed, for example neutrophils or neutrophil-like cultured cells into which a calgranulin gene has been introduced, an appropriate concentration of sample which may contain a substance inhibiting or activating the granule secretion reaction is incubated for 1–30 minutes, for example. A water-soluble calcium compound is added at a concentration of, for example, 0.01–10 μM, and preferably 0.1–3 μM, and the mixture is incubated for 1–30 minutes, for example. Then calcium ionophore, for example, A23187 or ionomycin, is added at a concentration of 0.01–10 μM, and preferably 0.1–3 μM to initiate the granule secretion reaction.

Next, the step C) for detecting the subject substance secreted from the cell line is carried out.

Azurophil granules (primary granules), specific granules (secondary granules), and storage granules (tertiary granules) are given as granules contained in neutrophils. Acidic β-glycerophosphatase, β-glucuronidase, N-acetyl-β-glucurosaminidase, α-mannosidase, arylsulfatase, β-galactosidase, α-fucosidase, cathepsin B, cathepsin D, cathepsin G, elastase, proteinase 3, myeloperoxidase, lysozyme, and the like are secreted from Azurophil granules. Collagenase, lysozyme, lactoferrin, vitamin $B_{12}$-binding protein, cytochrome b, and the like are secreted from the special granules. Gelatinase, N-acetyl-β-glucurosaminidase, cathepsin B, cathepsin D, β-glucuronidase, β-glycerophosphatase, α-mannosidase, and the like are secreted from storage granules. These substances can be selected as a subject substance to be detected. Each of the subject substances can be quantitatively analyzed by means of an appropriate method.

For example, the quantity of myeloperoxidase secreted from Azurophil granules can be determined from the rate of increase in the absorbance at 650 nm by a spectrophotometer using 3,3',5,5'-tetramethylbenzidine and a hydrogen peroxide as substrates. Lactoferrin secreted from specific granules can be determined by ELISA (enzyme-linked immunoassay, an assay kit manufactured by Oxis Co.) using an antilactoferrin antibody. The quantity of N-acetyl-β-glucurosaminidase, β-glucuronidase, and α-mannosidase secreted from storage granules can be determined by measuring 4-methylunberiferil which is produced by the hydrolysis of a 4-methylunberiferil derivative (Sigma Co.) as a substrate using fluorescence spectrophotometer at an excitation wavelength of 365 nm and a fluorescence wavelength 450 nm.

The method of detection of a substance which may inhibit or activate the granule secretion reaction according to the present invention can be carried out in this manner. Therefore, a substance which inhibits or activates the granule secretion reaction contained in the above-mentioned sample can be quantitatively determined.

A preferable example of the quantitative determination of the present invention is as follows.

The target substance (sample) which is an object of screening is caused to be present at an appropriate concentration in a suspension of neutrophils or neutrophil-like cultured cells having permeabilized cell membranes, and a calgranulin and a water-soluble calcium compound are added to make an appropriate concentration, respectively, to measure the amount of secreted granules. For example, $5 \times 10^6$ cells/ml to $5 \times 10^7$ cells/ml of human neutrophils which are treated with digitonin to make the membrane permeabilized membranes is prepared. A sample is added to a concentration of 1–100 μM, followed by the addition of calgranulin A (0.01–10 μM, preferably 0.1–3 μM) and an aqueous solution of calcium chloride compound (0.01–10 μM, preferably 0.1–3 μM). The mixture is incubated at 25–40° C., preferably 30–70° C., for 1–60 minutes, and preferably for 5–15 minutes. As examples of the medium used in this incubation buffer solution (pH: about 7–7.4) containing, 100 mM–200 mM potassium chloride, 10 mM–20 mM sodium chloride, and 0.3 mM–3 mM EGTA, for example, phosphoric acid, MOPS, HEPES, Tris, TAPA, BES, and TES buffer containing them can be given. The amount of the substance secreted during the incubation is determined and compared with a control to which no sample is added.

According to the present invention a method of screening a calgranulin activity activator, which is used for increasing calgranulin activity of neutrophils or neutrophil-like cultured cells and then increasing granule secretion, can be provided. Specifically, a substance (sample) which is an object of the screening is selected and caused to be present in a suspension of neutrophils or neutrophil-like cultured cells having permeabilized cell membranes at an appropriate concentration (1–100 μM, for example). A water-soluble calcium compound at an appropriate concentration (for example, 0.01–10 μM, and preferably 0.1–3 μM) and a calgranulin, for example calgranulin A, at an appropriate concentration (for example, 0.01–10 μM, and preferably 0.1–3 μM) are added to the suspension, thereby screening the substance which increases the quantity of granules secretion even more.

A simple method of screening a calgranulin activity deactivator can be provided by the method of activating the activity of calgranulin permeable through cell membranes of neutrophils or neutrophil-like cultured cells of the present invention. Specifically, a substance (sample) which is an object of screening is selected and caused to be present in a suspension of cultured neutrophils or neutrophil-like cells at an appropriate concentration (1–100 µM, for example). A calgranulin activity activator at an appropriate concentration (for example, 0.01–100 µM, and preferably 0.1–10 µM) is added to the suspension, thereby screening the substance which inhibits granules secretion.

Granule secretion of neutrophils is known to injure intima of blood vessels as mentioned above. Injury of blood vessel intima is known to be deeply associated with diseases such as adult respiratory distress syndrome (ARDS), injury by reperfusion after ischemia during acute myocardial infarction, glomerular nephritis, cystic fibrosis, rheumatoid arthritis, chronic bronchitis, cerebral vasospasm, asthma, peripheral circulation disorder, angina pectoris, hypertension, arteriosclerosis, and the like. Therefore, the above method of screening the neutrophil granule secretion inhibitor can be applied to the screening of a substance which inhibits the intimal injury of blood vessels.

BEST MODE FOR CARRYING OUT THE INVENTION

The present invention will now described more specifically by way of examples. However, the present invention is not limited to these following examples.

EXAMPLE 1

Method of Controlling Elastase Secretion From Human Neutrophils According to an Increase or Decrease of Calgranulin Content Elastase is a typical secretion substance which is present in primary granules of neutrophils. Elastase is a proteinase which decomposes elastin, an elastic protein present in blood vessels., etc., and causes hindrance to occur. A method of controlling elastase secretion by calgranulin using human neutrophils will be described.

A neutrophil suspension was prepared from blood collected from human vein according to the method described in Biological Chemistry Experiment Lecture, second series, No. 8, Blood, Vol. 2, 679–685). The neutrophil suspension was adjusted to a concentration of $1 \times 10^7$ cells/ml in a plastic test tube using a permeabilized buffer (PB) (30 mM HEPES, 100 mM KCl, 20 mM NaCl, 1 mM EGTA, pH 7.0) and incubated at 37° C. for 10 minutes. Digitonin (Sigma company) was added to the neutrophil suspension to a final concentration of 5–7.5 µg/ml and the mixture was incubated at, 37° C. for 15 minutes. The neutrophil suspension was centrifuged at 1200 rpm for 5 minutes. After discarding supernatant, precipitated neutrophils were re-suspended in PB to prepare a permeabilized neutrophil suspension (cell concentration: $1 \times 10^7$/ml).

The permeabilized neutrophil suspension was added to a 96-well immunoplate, 200 µl per well, and incubated for at 37° C. 15 minutes. Next, an aqueous solution of calcium chloride (final concentration: 1 µM)/and calgranulin A, calgranulin B, or a equimolar mixture of calgranulin A and calgranulin B (each to a final concentration of 0 µM, 0.3 µM, 1 µM, or 3 µM) were added, and the resulting mixture was incubated at 37° C. for 5 minutes.

The 96-well immunoplate was centrifuged at 1200 rpm for one minute at 4° C. using a centrifugation container for immunoplates. The supernatant is transferred to another 96-well immunoplate, 160 µl per well, and incubated at 37° C. for 5 minutes. 10 mM of an elastase substrate (Suc-Ala-Pro-Ala-pNA, Peptide Laboratory, Inc.) was added to the 96-well immunoplate. After gently shaking, the mixture was incubated at 37° C. for 30 minutes. Then, absorbance at 405 nm was measured using a microplate reader.

Figure 1:
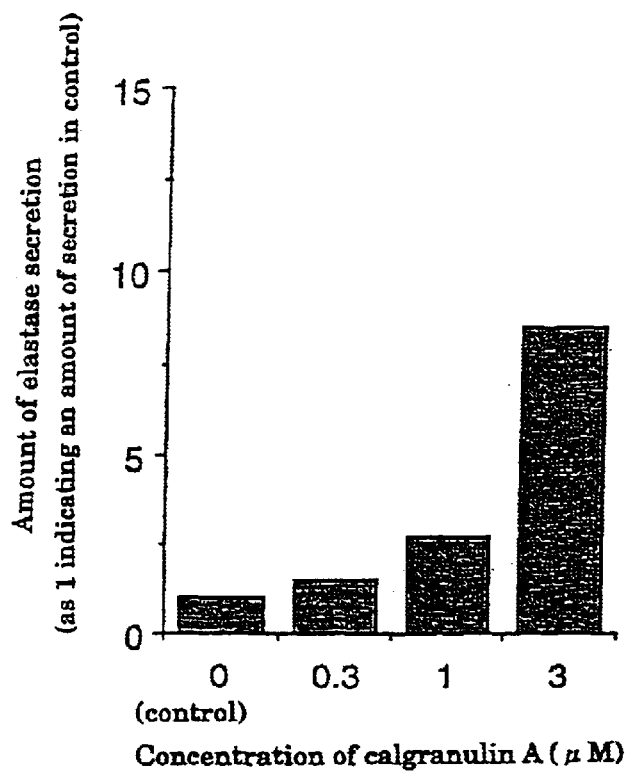
FIG. 1 shows an elastase secretion reaction of human neutrophils having high permeability cell membranes by calgranulin A in Example 1.
Figure 2:
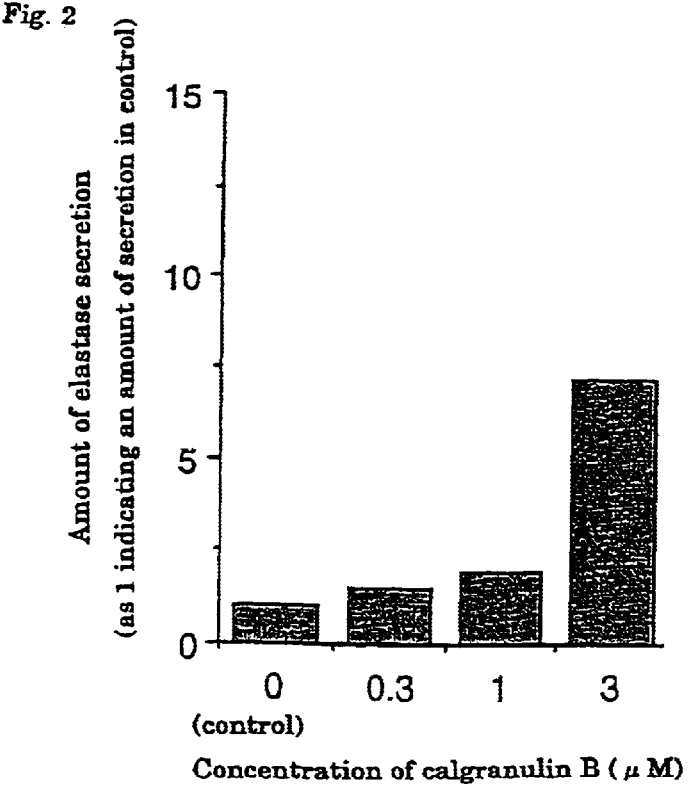
FIG. 2 shows an elastase secretion reaction of human neutrophils having high permeability cell membranes by calgranulin B in Example 1.
Figure 3:
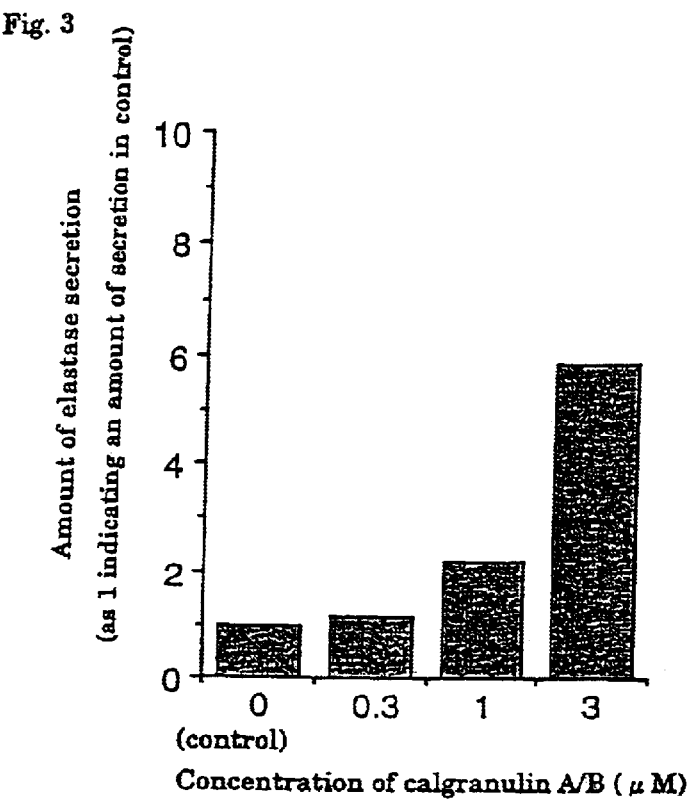
FIG. 3 shows an elastase secretion reaction of human neutrophils having high permeability cell membranes by a mixture of calgranulin A and calgranulin B in Example 1.

The results are shown in FIG. 1 (calgranulin A), FIG. 2 (calgranulin B), and FIG. 3 (a mixture of calgranulin A and calgranulin B). Calgranulin A increased elastase secretion from, neutrophils if the amount of addition is increased to increase the calgranulin activity (FIG. 1). Assuming that the amount of elastase secretion in the absence of calgranulin A is 1, 3 µM of calgranulin A remarkably increased the amount of elastase secretion (about eight times).

Calgranulin B increased elastase secretion from neutrophils if the amount of addition is increased to increase the calgranulin activity (FIG. 2). Assuming that the amount of elastase secretion in the absence of calgranulin B is 1, 3 µM of calgranulin B remarkably increased the amount of elastase secretion (about seven times). A mixture of calgranulin A and calgranulin B increased elastase secretion from neutrophils if the amount of addition is increased to increase the calgranulin activity (FIG. 3). Assuming that the amount of elastase secretion in the absence of the mixture is 1, 3 µM of the mixture of calgranulin A and calgranulin B remarkably increased the amount of elastase secretion (about six times).

These results show that change in the amount of calgranulin A, calgranulin B, or a mixture of calgranulin A and calgranulin B in neutrophils can remarkably change the amount of elastase secretion.

EXAMPLE 2

Method of Controlling Lactoferrin Secretion From Human Neutrophils According to an Increase or Decrease of Calgranulin Content Lactoferrin is a typical secretion substance which is present in secondary granules of neutrophils. A method of controlling lactoferrin secretion by calgranulin using human neutrophils will be described.

A neutrophil suspension was prepared from blood collected from human vein according to the method described in Biological Chemistry Experiment Lecture, second series, No. 8, Blood, Vol. 2, 679–685). The neutrophil suspension was adjusted to a concentration of $1\times10^7$ cells/ml using PB in a plastic test tube and incubated at 37° C. for 10 minutes. Digitonin (Sigma company) was added to the neutrophil suspension to a final concentration of 5 µg/ml and the mixture was incubated at 37° C. for 15 minutes.

Figure 4:
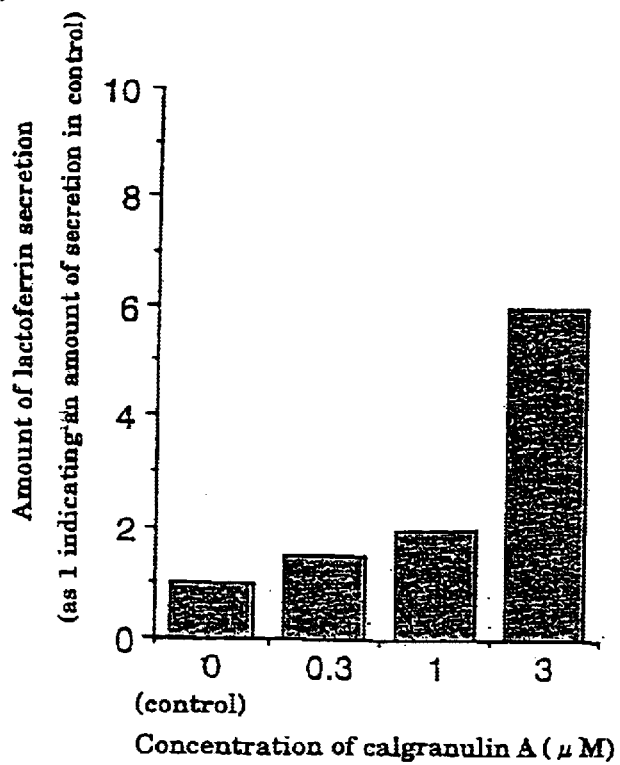
FIG. 4 shows a lactoferrin secretion reaction of human neutrophils having high permeability cell membranes by calgranulin A in Example 2.
Figure 5:
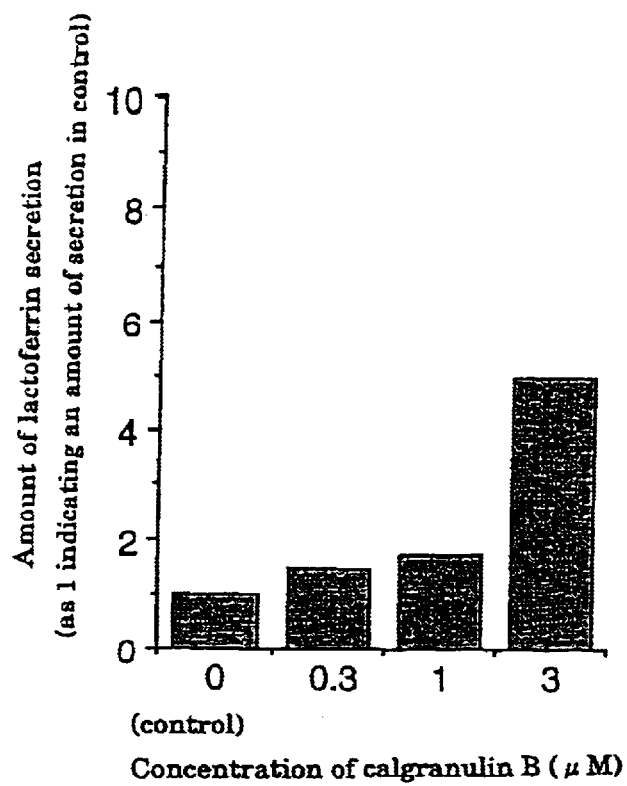
FIG. 5 shows a lactoferrin secretion reaction of human neutrophils having high permeability cell membranes by calgranulin B in Example 2.
Figure 6:
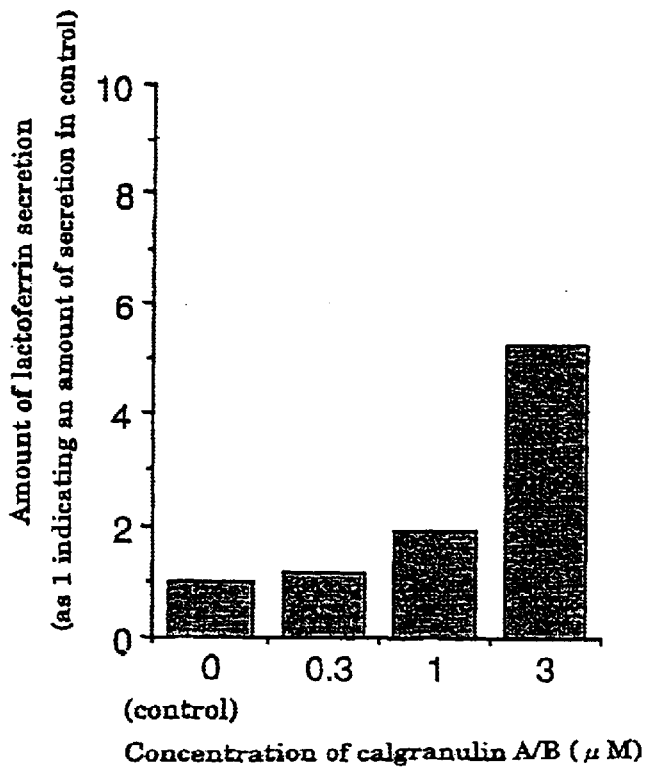
FIG. 6 shows a lactoferrin secretion reaction of human neutrophils having high permeability cell membranes by a mixture of calgranulin A and calgranulin B in Example 2.

The neutrophil suspension was centrifuged at 1200 rpm for 5 minutes. After supernatant was discarded, precipitated neutrophils were re-suspended in PB to prepare a permeabilized neutrophil suspension (cell concentration: $1\times10^7$ cells/ml). The permeabilized neutrophil suspension was added to a 96-well immunoplate, 200 µl per well, and incubated at 37° C. for 15 minutes. Next, an aqueous solution of calcium chloride (final concentration: 1 µM) and calgranulin A, calgranulin B, or a equimolar mixture of calgranulin A and calgranulin B (each to a final concentration of 0 µM, 0.3 µM, 1 µM, or 3 µM) were added, and the resulting mixtures were incubated at 37° C. for 5 minutes. The 96-well immunoplate was centrifuged at 1200 rpm for one minute at 4° C. ELISA-kit (OXIS Co.) was used for the determination of lactoferrin. The results are shown in FIGS. 4, 5, and 6. Calgranulin A increased lactoferrin secretion from neutrophils if the amount of addition is increased to increase the calgranulin activity (FIG. 4). Assuming that the amount of lactoferrin secretion in the absence of calgranulin A is 1, 3 µM of calgranulin A remarkably increased the amount of lactoferrin secretion (about six times). Calgranulin B increased lactoferrin secretion from neutrophils if the amount of addition is increased to increase the calgranulin activity (FIG. 5). Assuming that the amount of lactoferrin secretion in the absence of calgranulin B is 1, 3 µM of calgranulin B remarkably increased the amount of lactoferrin secretion (about five times). A mixture of calgranulin A and calgranulin B increased lactoferrin secretion from neutrophils if the amount of addition is increased to increase the calgranulin activity (FIG. 6). Assuming that the amount of lactoferrin secretion in the absence of the mixture is 1, 3 µM of the mixture of calgranulin A and calgranulin B remarkably increased the amount of lactoferrin secretion (about five times).

These results show that change in the amount of calgranulin A, calgranulin B, or a mixture of calgranulin A and calgranulin B in neutrophils can remarkably change the amount of lactoferrin secretion.

The results of Examples 1 and 2 show that calgranulins are important proteins to control granule secretion form neutrophils.

EXAMPLE 3

Method of Screening a Substance Inhibiting or Activating Granule Secretion by Allowing a Sample to Stand in the System in Which the Amount of Elastase Secretion From Neutrophils is Greatly Increased by Changing Calgranulin Activity A neutrophil suspension was prepared from blood collected from a human vein according to the method described in Biological Chemistry Experiment Lecture, second series, No. 8, Blood, Vol. 2, 679–685). The neutrophil suspension was adjusted to a concentration of $1\times10^7$ cells/ml using PB in a plastic test tube and incubated at 37° C. for 10 minutes. Digitonin was added to the neutrophil suspension to a final concentration of 5 µg/ml and the mixture was incubated at 37° C. for 15 minutes. The neutrophil suspension was centrifuged at 1200 rpm for 5 minutes.

After supernatant was discarded, the precipitate was re-suspended in PB to prepare a permeabilized neutrophil suspension (cell concentration: $1\times10^7$ cells/ml). The permeabilized neutrophil suspension was added to a 96-well immunoplate, 200 µl per well, and incubated at 37° C. for 15 minutes. N-(4-methoxybenzyl)-N-(4-methoxyphenyl)-7-piperazinylheptyl amine trihydrochloride (Compound 1), N-benzyl-N-(4-methoxyphenyl)-7-piperazinylheptylamine trihydrochloride (Compound 2), 1,1-(di-4-hydroxyphenyl)-2-ethyl-1-octaene (Compound 3), and 2-hydroxy-5-((-4-((-2-pyridinylamino)sulfonyl)phenyl)azo)benzoic acid (Compound 4) were used as samples for screening.

These samples were added to a final concentration of 30 µM and the mixtures were incubated at 37° C. for 15 minutes. Next, an aqueous solution of calcium chloride (final concentration: 1 µM) and calgranulin A, calgranulin B, or a equimolar mixture of calgranulin A and calgranulin B (each to a final concentration of 0 µM, 0.3 µM, 1 µM, or 3 µM) were added, and the resulting mixtures were incubated at 37° C. for 5 minutes. The 96-well immunoplate was centrifuged at 1200 rpm for one minute at 4° C. using a centrifugal separator for immunoplates. The supernatant is transferred to another 96-well immunoplate and incubated at 37° C. for 5 minutes. 10 mM of an elastase substrate (Suc-Ala-Pro-Ala-pNA) was added to the 96-well immunoplate. After gently shaking, the mixture was incubated at 37° C. for 30 minutes. Then, absorbance at 405 nm was measured using a microplate reader.

The results are shown in Table 1. The secretion inhibiting rate of samples was determined by comparison with a control which does not contain the screening sample, assuming that the secretion from the control is 100%. Compound 1 and Compound 2 decreased the activity of calgranulin A and remarkably controlled granule secretion in a system in which the amount of elastase secretion from neutrophils has been remarkably decreased. Compound 3 remarkably increased the amount of secretion in the above system.

TABLE 1

| Name of sample | Amount of secretion (%) |
|---|---|
| Control | 100 |
| Compound 1 | 61 |
| Compound 2 | 51 |
| Compound 3 | 151 |
| Compound 4 | 75 |

INDUSTRIAL APPLICABILITY

The present invention is a very useful method of controlling granule secretion from neutrophils. The detecting method, screening method, or quantitative determination method of substances inhibiting or activating granule secretion based on the above method is very useful in providing therapeutic drugs for various diseases due to intimal injury of blood vessels brought about by granules secretion of neutrophil.

What is claimed is:

1. A method of controlling granule secretion comprising performing a treatment to increase or decrease a calcium binding form of at least one of a peptide (i) and a peptide (ii) on a cell line having granule secretion capability, thereby to increase or decrease granule secretion from the cell line, wherein peptide (i) consists of amino acids 1–93 of SEQ ID NO: 3 and peptide (ii) consists of amino acids 1–114 of SEQ ID NO:4.

2. The method according to claim 1, wherein the cell line having granule secretion capability is neutrophils or neutrophil-like cultured cells originating from a warm-blooded animal, said neutrophil-like culture cells containing at least one type of granule included in neutrophils.

3. A method of detecting a target substance inhibiting or activating a granule secretion reaction in a cell line, comprising:

A) increasing a calcium binding form of at least one of a peptide (i) and a peptide (ii) in cell lines having granule secretion capability, wherein peptide (i) consists of amino acids 1–93 of SEQ ID NO: 3 and peptide (ii) consists of amino acids 1–114 of SEQ ID NO: 4;

B) causing a sample which is suspected to contain said target substance to contact with the cell lines having granule secretion capability after or during step A);

C) incubating a mixture resulting after step A and step B are carried out; and

D) detecting a material secreted from the cell line.

4. The method according to claim 3, wherein the cell line having granule secretion capability is neutrophils or neutrophil-like cultured cells originating from a warm-blooded animal, said neutrophil-like culture cells containing at least one type of granule included in neutrophils.

5. The method according to claim 3, wherein the method of detection is a quantitative determination method.

6. The method according to claim 3, wherein the method of detection is a screening method.

7. A method of obtaining a candidate substance for controlling intimal injury of blood vessels comprising acquiring the candidate substance for controlling intimal injury of blood vessels by screening for a target substance inhibiting granule secretion reaction by the method of claim 6.

8. The method according to claim 3, wherein step A) comprises successively carrying out the following steps a) and b):
   a) changing the cell line having granule secreting capability into a permeabilized cell; and
   b) simultaneously or successively adding at least one of peptide (i) and peptide (ii) and a water-soluble calcium compound to the cell line and incubating the cell line.

9. The method according to claim 8, wherein the water-soluble calcium compound comprises calcium ions at a final concentration of 0.01–10 µM.

10. The method according to claim 8, wherein the cell line having granule secretion capability is neutrophils or neutrophil-like cultured cells originating from a warm-blooded animal, said neutrophil-like culture cells containing at least one type of granule included in neutrophils.

11. A method of detecting a target substance inhibiting or activating a granule secretion reaction, comprising the steps of:
   A) causing a sample which is suspected to contain said target substance to contact with the cell lines having granule secretion capability;
   B) increasing a calcium binding form of at least one of a peptide (i) and a peptide (ii) in cell lines having granule secretion capability, wherein peptide (i) consists of amino acids 1–93 of SEQ ID NO: 3 and peptide (ii) consists of amino acids 1–114 of SEQ ID NO: 4;
   C) incubating a mixture resulting after step A and step B are carried out; and
   D) detecting a material secreted from the cell line.

12. The method according to claim 11, wherein step B) comprises successively carrying out the following steps a) and b):
   a) converting the cell line having granule secreting capability into a permeabilized cell line; and
   b) simultaneously or successively adding peptide (i) and/or peptide (ii) and a water-soluble calcium compound to the cell line and incubating the cell line.

13. The method according to claim 12, wherein the cell line having granule secretion capability is neutrophils or neutrophil-like cultured cells originating from a warm-blooded animal, said neutrophil-like culture cells containing at least one type of granule included in neutrophils.

14. The method according to claim 11, wherein the cell line having granule secretion capability is neutrophils or neutrophil-like cultured cells originating from a warm-blooded animal, said neutrophil-like culture cells containing at least one type of granule included in neutrophils.

15. The method according to claim 12, wherein the water-soluble calcium ions are at a final concentration of 0.01–10 µM.

16. The method according to claim 11, wherein the method of detection is a quantitative determination method.

17. The method according to claim 11, wherein the method of detection is a screening method.

18. A method of obtaining a candidate substance for controlling intimal injury of blood vessels comprising acquiring the candidate substance for controlling intimal injury of blood vessels by screening for a target substance inhibiting granule secretion reaction by the method of claim 17.

* * * * *

SEQUENCE LISTING

<160> NUMBER OF SEQ ID NOS: 4

<210> SEQ ID NO 1
<211> LENGTH: 282
<212> TYPE: DNA
<213> ORGANISM: Homo sapiens
<220> FEATURE:
<221> NAME/KEY: CDS
<222> LOCATION: (1)..(279)

<400> SEQUENCE: 1

```
atg ttg acc gag ctg gag aaa gcc ttg aac tct atc atc gac gtc tac      48
Met Leu Thr Glu Leu Glu Lys Ala Leu Asn Ser Ile Ile Asp Val Tyr
  1               5                  10                  15 cac aag tac tcc ctg ata aag ggg aat ttc cat gcc gtc tac agg gat      96
His Lys Tyr Ser Leu Ile Lys Gly Asn Phe His Ala Val Tyr Arg Asp
             20                  25                  30 gac ctg aag aaa ttg cta gag acc gag tgt cct cag tat atc agg aaa     144
Asp Leu Lys Lys Leu Leu Glu Thr Glu Cys Pro Gln Tyr Ile Arg Lys
         35                  40                  45 aag ggt gca gac gtc tgg ttc aaa gag ttg gat atc aac act gat ggt     192
Lys Gly Ala Asp Val Trp Phe Lys Glu Leu Asp Ile Asn Thr Asp Gly
     50                  55                  60 gca gtt aac ttc cag gag ttc ctc att ctg gtg ata aag atg ggc gtg     240
Ala Val Asn Phe Gln Glu Phe Leu Ile Leu Val Ile Lys Met Gly Val
 65                  70                  75                  80 gca gcc cac aaa aaa agc cat gaa gaa agc cac aaa gag tag             282
Ala Ala His Lys Lys Ser His Glu Glu Ser His Lys Glu
                 85                  90
```

<210> SEQ ID NO 2
<211> LENGTH: 345
<212> TYPE: DNA
<213> ORGANISM: Homo sapiens
<220> FEATURE:
<221> NAME/KEY: CDS
<222> LOCATION: (1)..(342)

<400> SEQUENCE: 2

```
atg act tgc aaa atg tcg cag ctg gaa cgc aac ata gag acc atc atc      48
Met Thr Cys Lys Met Ser Gln Leu Glu Arg Asn Ile Glu Thr Ile Ile
  1               5                  10                  15 aac acc ttc cac caa tac tct gtg aag ctg ggg cac cca gac acc ctg      96
Asn Thr Phe His Gln Tyr Ser Val Lys Leu Gly His Pro Asp Thr Leu
             20                  25                  30 aac cag ggg gaa ttc aaa gag ctg gtg cga aaa gat ctg caa aat ttt     144
Asn Gln Gly Glu Phe Lys Glu Leu Val Arg Lys Asp Leu Gln Asn Phe
         35                  40                  45 ctc aag aag gag aat aag aat gaa aag gtc ata gaa cac atc atg gag     192
Leu Lys Lys Glu Asn Lys Asn Glu Lys Val Ile Glu His Ile Met Glu
     50                  55                  60 gac ctg gac aca aat gca gac aag cag ctg agc ttc gag gag ttc atc     240
Asp Leu Asp Thr Asn Ala Asp Lys Gln Leu Ser Phe Glu Glu Phe Ile
 65                  70                  75                  80 atg ctg atg gcg agg cta acc tgg gcc tcc cac gag aag atg cac gag     288
Met Leu Met Ala Arg Leu Thr Trp Ala Ser His Glu Lys Met His Glu
                 85                  90                  95 ggt gac gag ggc cct ggc cac cac cat aag cca ggc ctc ggg gag ggc     336
Gly Asp Glu Gly Pro Gly His His His Lys Pro Gly Leu Gly Glu Gly
            100                 105                 110 acc ccc taa                                                         345
```

```
Thr Pro

<210> SEQ ID NO 3
<211> LENGTH: 93
<212> TYPE: PRT
<213> ORGANISM: Homo sapiens

<400> SEQUENCE: 3

Met Leu Thr Glu Leu Glu Lys Ala Leu Asn Ser Ile Ile Asp Val Tyr
 1               5                  10                  15

His Lys Tyr Ser Leu Ile Lys Gly Asn Phe His Ala Val Tyr Arg Asp
             20                  25                  30

Asp Leu Lys Lys Leu Leu Glu Thr Glu Cys Pro Gln Tyr Ile Arg Lys
             35                  40                  45

Lys Gly Ala Asp Val Trp Phe Lys Glu Leu Asp Ile Asn Thr Asp Gly
     50                  55                  60

Ala Val Asn Phe Gln Glu Phe Leu Ile Leu Val Ile Lys Met Gly Val
 65                  70                  75                  80

Ala Ala His Lys Lys Ser His Glu Glu Ser His Lys Glu
                 85                  90

<210> SEQ ID NO 4
<211> LENGTH: 114
<212> TYPE: PRT
<213> ORGANISM: Homo sapiens

<400> SEQUENCE: 4

Met Thr Cys Lys Met Ser Gln Leu Glu Arg Asn Ile Glu Thr Ile Ile
 1               5                  10                  15

Asn Thr Phe His Gln Tyr Ser Val Lys Leu Gly His Pro Asp Thr Leu
             20                  25                  30

Asn Gln Gly Glu Phe Lys Glu Leu Val Arg Lys Asp Leu Gln Asn Phe
             35                  40                  45

Leu Lys Lys Glu Asn Lys Asn Glu Lys Val Ile Glu His Ile Met Glu
     50                  55                  60

Asp Leu Asp Thr Asn Ala Asp Lys Gln Leu Ser Phe Glu Glu Phe Ile
 65                  70                  75                  80

Met Leu Met Ala Arg Leu Thr Trp Ala Ser His Glu Lys Met His Glu
                 85                  90                  95

Gly Asp Glu Gly Pro Gly His His Lys Pro Gly Leu Gly Glu Gly
                100                 105                 110

Thr Pro
```